United States Patent [19]

De Coster

[11] Patent Number: Plant 6,098

[45] Date of Patent: Feb. 2, 1988

[54] PHILODENDRON PLANT NAMED RUBY

[76] Inventor: Paul De Coster, Brusselsesteenweg 94, 9230 Melle, Belgium

[21] Appl. No.: 815,075

[22] Filed: Dec. 27, 1985

[51] Int. Cl.[4] ..... A01H 5/00
[52] U.S. Cl. ..... Plt./88
[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A philodendron plant named Ruby having dark green-brown foliage at top of plant, changing to dark green as leaves mature and new growth appears at top; vertical, fast a vigorous growth habit; grey-purple petioles, stem and petiole sheath providing a striking contrast with dark foliage; relatively short internodes which produce an abundance of foliage, and by its ease of propagation by tissue culture.

1 Drawing Figure

The present invention comprises a new and distinct cultivar of philodendron plant named Ruby.

The new cultivar was discovered growing among several hundred random seedlings obtained in approximately September of 1977 from Bamboo Nursery, Opapka, Fla. The plants were approximately 3–4" long with roots, but not rooted in soil, and were indistinguishable one from the other at the time of purchase. The parentage of the new cultivar was not known at the time of acquisition, nor is it now known.

When the seedlings were grown to mature plants by applicant in Melle, Belgium, in the greenhouses of applicant, the novel characteristics of the new cultivar were readily evident. Asexual reproduction by me of the new cultivar by tissue culture beginning in approximately 1982 in Melle, Belgium, and repeated asexual reproduction thereafter, has demonstrated that Ruby retains its distinctive characteristics through successive propagation.

The following characteristics in combination distinguish Ruby from other philodendron cultivars of this general type.

1. At the top of the plant, immature leaves are a dark green-brown, similar to the leaf color of Royal Queen, disclosed in U.S. Plant Pat. No. 3,396. When the leaves mature, they become a dark green. The dark green-brown color gives an appearance tending toward black.
2. Vertical growth habit, with the plant normally being attached to a moss pole or similar support to better express the vertical growth.
3. Relatively short internodes for a vertically grown cultivar, thereby producing an abundance of foliage.
4. A fast and vigorous grower, resulting in a strong plant.
5. The mature petiole color is deep grey-purple, similar to the color of the main stem. Immature petioles are orange-brown infused with purple.
6. The petiole sheath is a lighter grey-purple, and together with the stem and petiole color, provides a striking contrast with the foliage.
7. Propagates very efficiently by tissue culture.

The color photographic drawing is a front view of a plant of Ruby, approximately ten (10) months old. The photograph was taken when the plant was not in flower.

The following observations and measurements are based on plants of Ruby ten (10) months in age grown in 25 cm. pots in Melle, Belgium in greenhouses in accordance with standard commercial practices. Color values are based on The Royal Horticultural Society Colour Chart (R.H.S.), with the color values being taken in November at approximately 3:00 p.m. under natural light conditions.

FORM CHARACTERISTICS

Leaf shape:

*Mature.*—Generally elliptic, with bottom of leaf being concavely shaped at petiole connecter; undulating or wavy in direction of length, particularly at edge.

*Immature.*—Generally ovate, with bottom of leaf at petiole connecter being slightly concave.

*Tip.*—Cuspidate.

*Base.*—Concavely shaped relative to rib; sagittate.

*Margin.*—Smooth.

*Veination.*—Present, generally pinnate.

Leaf attachment: Stalked.

Leaf arrangement: Alternate.

Petiole: Rigid, extending when immature generally more vertical than horizontal in center of plant; round except flat on inner surface.

Stem: Short, internodes 5–6 cm.

Overall appearance: Self-branching; abundant vertical and symmetrical foliage.

SIZE CHARACTERISTICS OF TYPICAL COMMERCIAL PLANT

Leaf:

*Width at widest point.*—14–17 cm.

*Width* 1" from top.—3–4 cm.

*Length.*—25–30 cm.

Petiole:

*Length.*—20–24 cm. for mature leaves.

*Diameter (center).*—Approximately 1–1.5 cm. at base of internodes; petioles are grooved.

*Internode spacing.*—Approximately 5–6 cm.

Petiole sheath: 12–15 cm.

COLOR CHARACTERISTICS

Leaf:

*Mature (green).*—Upper surface 147A; under surface 148A, with infusing of 183A-B around edge and veins; central rib and veins approximately 183A.

*Mature* (*green-brown*).—Upper surface much deeper than 147A, appearing green-black for which there is no color value; lower surface 148A, with infusing of 183A-B at edge and around veins.

*Immature.*—Color incapable of being valued; heavy infusion of deep purple with medium dark green gives the appearance of green-purple.

Main stem: 177A, infused with purple.

Petiole:

*Mature.*—187A.

*Immature.*—177A, infused with purple.

Petiole sheath: Outside, 183C-D; inside, 185D.

I claim:

1. A new and distinct cultivar of philodendron plant named Ruby, as illustrated and described, and particularly characterized by the combined features of dark green-brown foliage at top of plant, changing to dark green as leaves mature and new growth appears at top; vertical, fast and vigorous growth habit; grey-purple petioles, stem and petiole sheath provide a striking contrast with dark foliage; relatively short internodes produce an abundance of foliage, and by its ease of propagation by tissue culture.

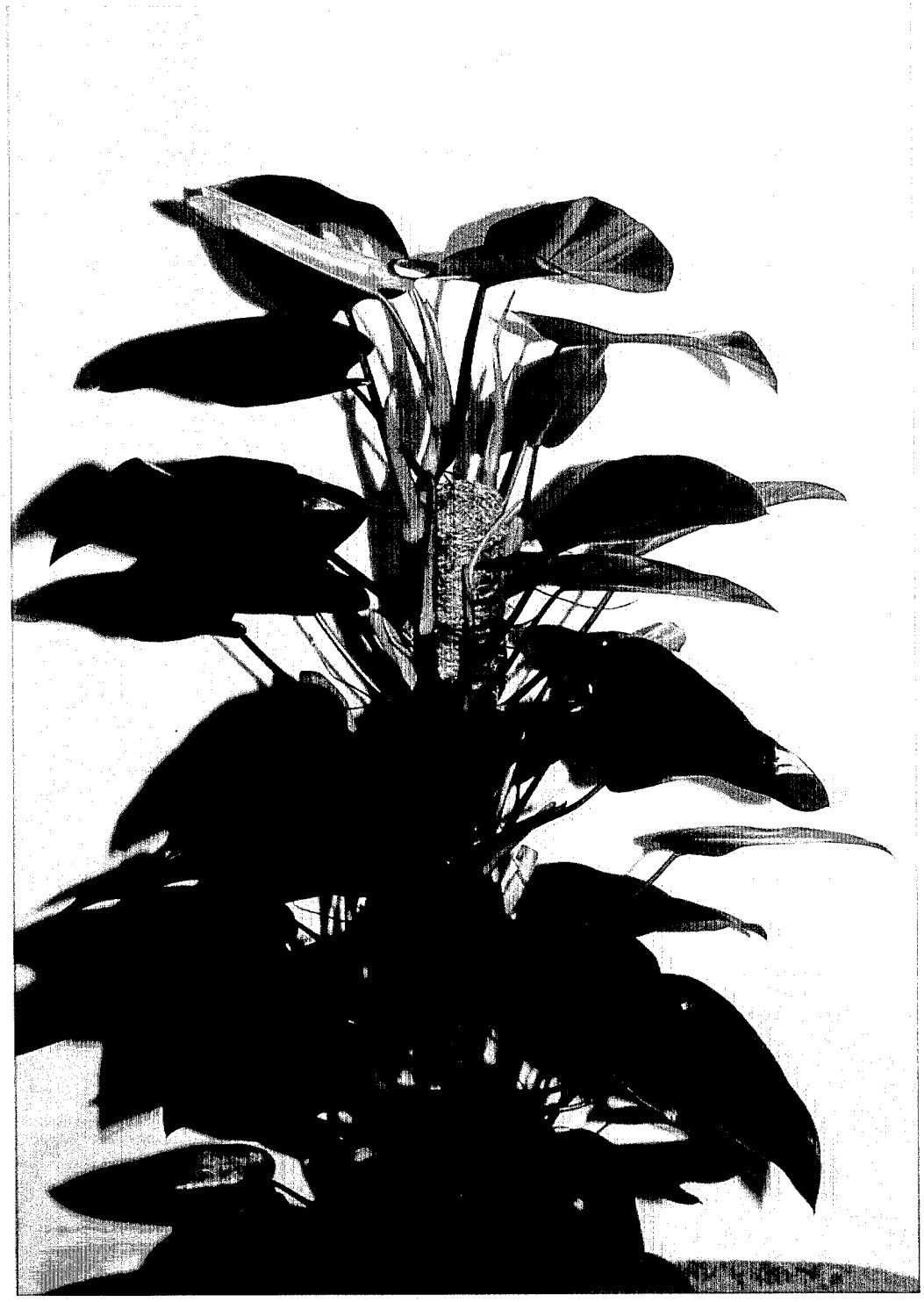

* * * * *